(12) United States Patent
Elsner

(10) Patent No.: US 10,507,082 B2
(45) Date of Patent: Dec. 17, 2019

(54) IMPRESSION JIG ASSEMBLY

(71) Applicant: ELSNER LLC, Wilmington, DE (US)

(72) Inventor: Edvin Elsner, Devecser (HU)

(73) Assignee: Elsner Global LLC, Charlestown, Nevis (KN)

( * ) Notice: Subject to any disclaimer, the term of this patent is extended or adjusted under 35 U.S.C. 154(b) by 0 days.

(21) Appl. No.: 15/905,945

(22) Filed: Feb. 27, 2018

(65) Prior Publication Data

US 2018/0243053 A1 Aug. 30, 2018

Related U.S. Application Data

(60) Provisional application No. 62/464,459, filed on Feb. 28, 2017.

(51) Int. Cl.
*A61C 8/00* (2006.01)

(52) U.S. Cl.
CPC ............ *A61C 8/0001* (2013.01); *A61C 8/006* (2013.01)

(58) Field of Classification Search
CPC ..... A61C 8/0001; A61C 8/006; A61C 8/0003; A61C 8/0068; A61C 8/0012; A61C 8/0066; A61C 8/0054
See application file for complete search history.

(56) References Cited

U.S. PATENT DOCUMENTS

| | | | | |
|---|---|---|---|---|
| 4,756,689 A | * | 7/1988 | Lundgren | A61C 8/005 433/169 |
| 5,125,840 A | * | 6/1992 | Durr | A61C 8/005 433/173 |

(Continued)

Primary Examiner — Nicholas D Lucchesi
(74) Attorney, Agent, or Firm — Jason D. Voight

(57) ABSTRACT

The impression jig comprises a main body having an inner channel and a head having an inner channel and adapted for being releasably attached to said main body, wherein the inner channel of the main body is provided with threads and at its lower end portion, with an inner positioning surface, and wherein the inner channel of the head is provided with threads and at its upper end portion, with an inner positioning surface. The impression jig further comprises a tubular screw adapted for guiding through the inner channel of the main body and the inner channel of the head, said tubular screw having an inner channel, and wherein the outer surface of the tubular screw is provided with first threads at an upper section thereof and with second threads at a predetermined distance from a lower section thereof. The impression jig further comprises a central screw, the shank of which can be guided through the inner channels of the tubular screw and the head, wherein a lower end portion of the shank is provided with threads, and the shank is longer than the total length of the main body and the head when engaged with each other. The impression jig further comprises a slide movable within the inner channel of the main body between a first position and a second position in an axial direction by means of said tubular screw, wherein the slide comprises a positioning surface on its outer side at a lower portion thereof. In its first position the slide resides partly in the main body and partly in the head, and the positioning surface of the slide engages with the upper positioning surface of the head in a form-fitting manner. In its second position the whole slide resides in the inner channel of the main body, and the positioning surface of the slide engages with the inner positioning surface of the main body.

3 Claims, 9 Drawing Sheets

(56) References Cited

U.S. PATENT DOCUMENTS

| | | | |
|---|---|---|---|
| 5,350,302 A * | 9/1994 | Marlin | A61C 8/0048 433/173 |
| 5,873,721 A * | 2/1999 | Willoughby | A61C 8/0001 433/173 |
| 6,227,856 B1 | 5/2001 | Beaty et al. | |
| 6,283,753 B1 | 9/2001 | Willoughby | |
| 6,290,499 B1 | 9/2001 | Lazzara et al. | |
| 6,332,777 B1 | 12/2001 | Sutter | |
| 9,681,930 B2 * | 6/2017 | Thome | A61C 8/0025 |
| 2003/0104336 A1 | 6/2003 | Sethi et al. | |
| 2010/0196855 A1 | 8/2010 | Müller et al. | |
| 2012/0028214 A1 | 2/2012 | Futterknecht et al. | |
| 2014/0087331 A1 * | 3/2014 | Hildmann | A61C 8/0025 433/174 |
| 2015/0313690 A1 * | 11/2015 | Elsner | A61C 8/0053 433/173 |
| 2016/0317253 A1 * | 11/2016 | Duerr | A61C 8/0054 |
| 2016/0367341 A1 * | 12/2016 | Perez Yanini | A61C 8/0001 |

\* cited by examiner

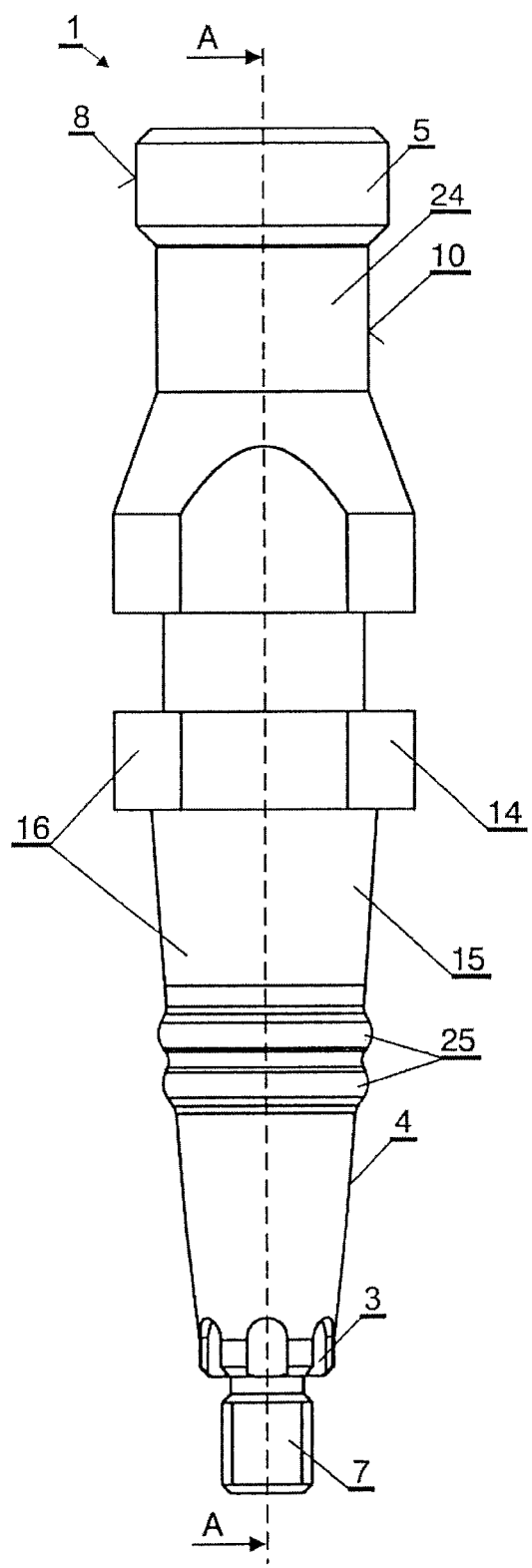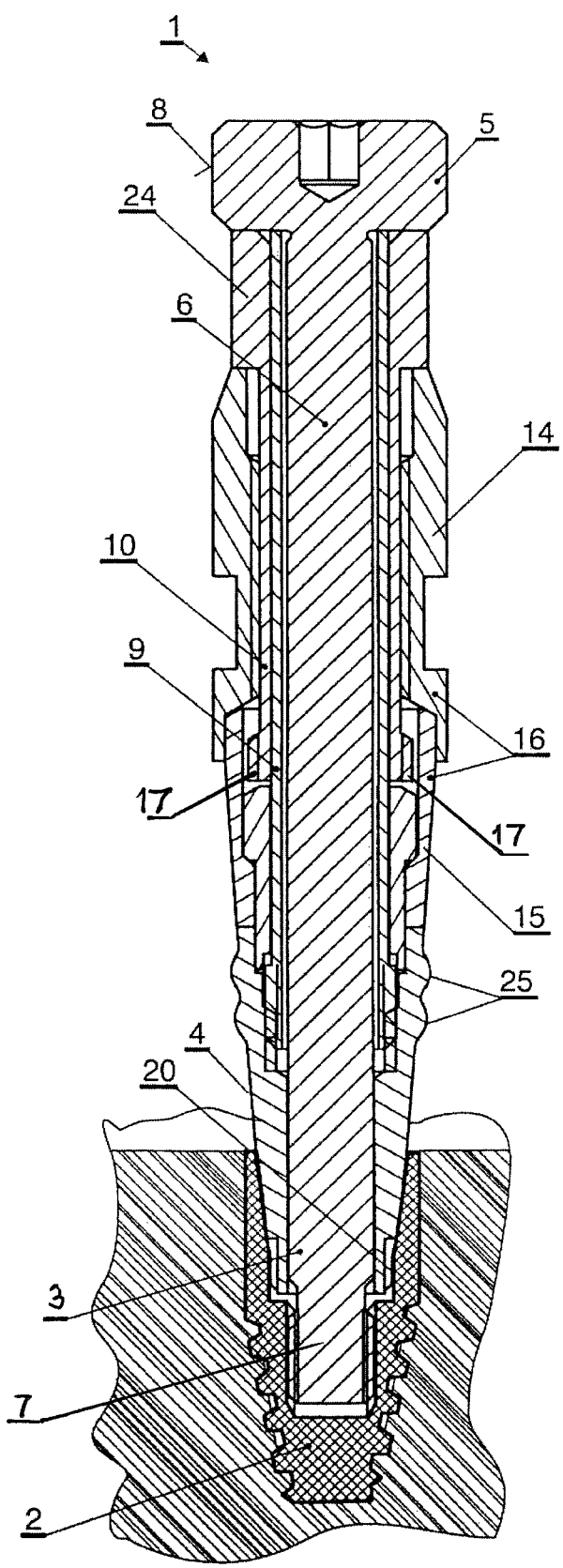
FIG. 1A
FIG. 1B

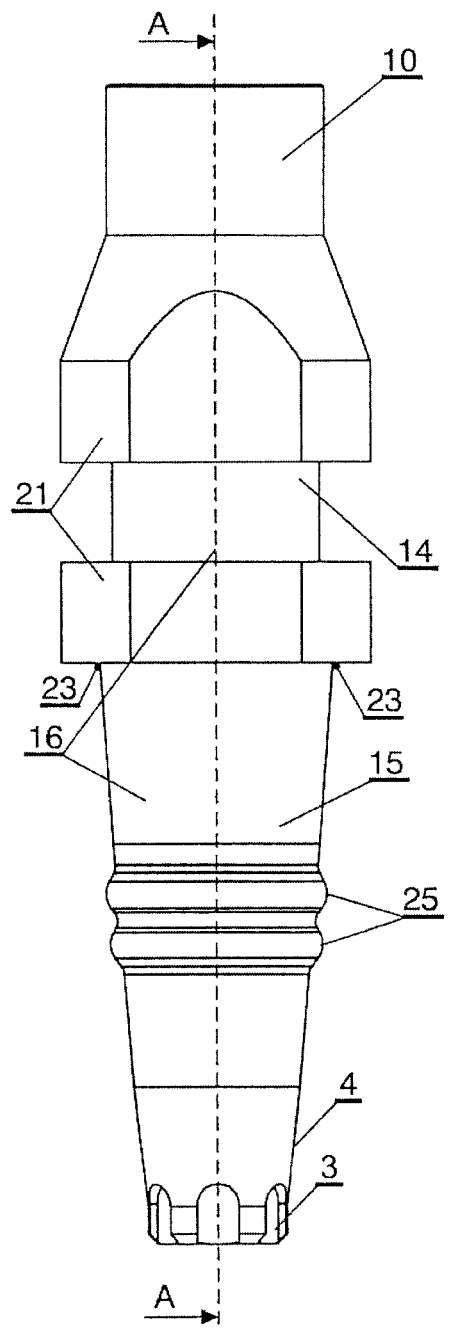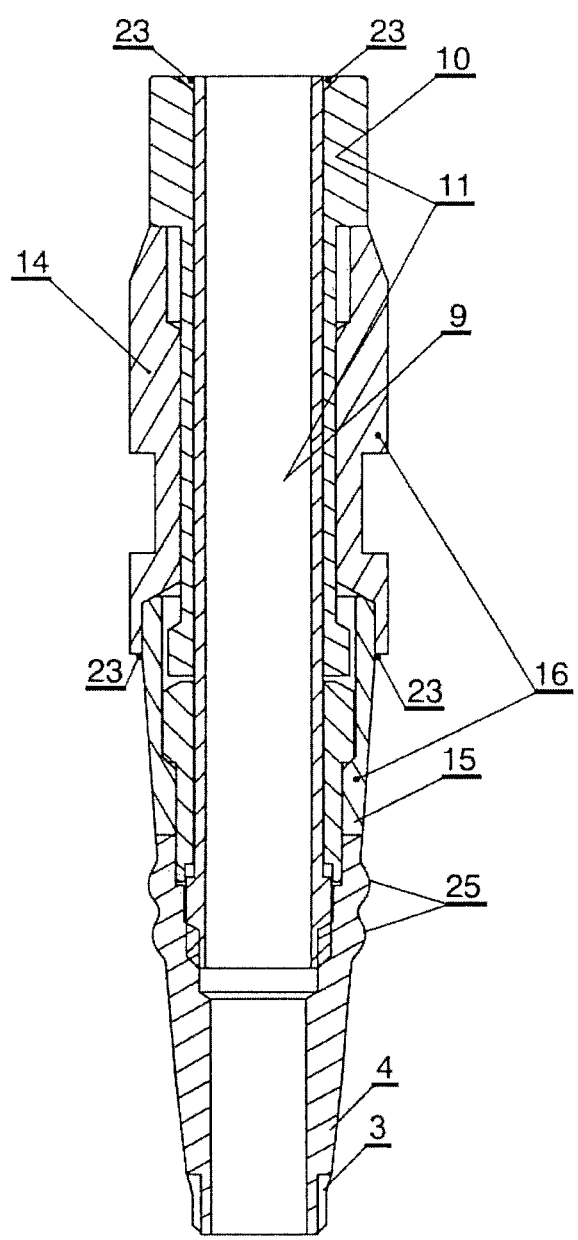
FIG. 8A
FIG. 8B

IMPRESSION JIG ASSEMBLY

This application claims priority to U.S. provisional application 62/464,459, filed Feb. 28, 2017, the disclosure of which is hereby incorporated by referenced herein.

The present invention relates to an impression jig for producing a dental implant.

With conventional impression jigs, the portion to be fitted into a dental implant is configured so that the stress-free removal of the impression jig from the dental implant can be carried out only in an axial direction of the impression jig. Such an impression jig is disclosed, for example, in documents EP 2213259 and WO 01/43659.

In the known impression jigs, the limited direction of removal of the jigs from the dental implants causes problems in particular when multiple impression jigs with different orientations are to be simultaneously removed from a group of dental implants. When multiple impression jigs with different orientations are removed in one direction at the same time, certain forces arise between the dental implants extending in different orientations and the impression jigs coupled thereto, which can damage the dental implants, the tissues around the implants and even the impression jigs themselves.

It is an object of the present invention to provide an impression jig that at its removal from a dental implant, significantly reduces the forces between the impression jig and the dental implant with respect to the known solutions, within a wide angular range of orientation of the implants and the impression jigs. The design and the operation of the impression jig according to the present invention will now be described in detail with reference to the drawings.

The invention is based on the inventive idea that if during the preparation of a sample, disengagement of the main body of the impression jig with respect to the head coupled to the implant is allowed by removing the impression jig from the implant and a minor displacement and/or rotation thereof relative to each other is also allowed, than the head moving within the dental implant exerts significantly lower forces to the inner surfaces of the implant. Since at the preparation of the sample, the main body and the head are mostly incorporated within a resilient sampling material, while moving the impression jig, the main body and the head can easily move with respect to each other. However, after the entire removal of the impression jig from the implant, the main body and the head can return into their initial axial orientation relative to each other due to the resiliency of the sampling material, so the impression jig is capable of perfectly copying the spatial orientation of the dental implant.

The above objects are achieved by providing an impression jig comprising a main body having an inner channel and a head having an inner channel and adapted for being releasably attached to said main body, wherein the inner channel of the main body is provided with threads and at its lower end portion, with an inner positioning surface, and wherein the inner channel of the head is provided with threads and at its upper end portion, with an inner positioning surface. The impression jig further comprises a tubular screw adapted for guiding through the inner channel of the main body and the inner channel of the head, said tubular screw having an inner channel, and wherein the outer surface of the tubular screw is provided with first threads at an upper section thereof and with second threads at a predetermined distance from a lower section thereof. The impression jig further comprises a central screw, the shank of which can be guided through the inner channels of the tubular screw and the head, wherein a lower end portion of the shank is provided with threads, and the shank is longer than the total length of the main body and the head when engaged with each other. The impression jig further comprises a slide movable within the inner channel of the main body between a first position and a second position in an axial direction by means of said tubular screw, wherein the slide comprises a positioning surface on its outer side at a lower portion thereof. In its first position the slide resides partly in the main body and partly in the head, and the positioning surface of the slide engages with the upper positioning surface of the head in a form-fitting manner. In its second position the whole slide resides in the inner channel of the main body, and the positioning surface of the slide engages with the inner positioning surface of the main body.

It is preferred that when the slide is in its first position, the first threaded part of the tubular screw engages with an upper threaded part of the main body.

It is preferred that when the slide is in its second position, the second threaded part of the tubular screw engages with the threads of the inner channel of the main body.

The design and the operation of the impression jig according to the present invention will now be described in detail with reference to the drawings.

FIG. 1A is a side view of an impression jig according to a preferred embodiment of the present invention in an assembled state.

FIG. 1B is a sectional view of the impression jig of FIG. 1a taken along the plane A-A, after its insertion into a dental implant.

FIGS. 8A and 8B are a side view and a sectional view, respectively, of the impression jig without the central screw.

Figure 2A:
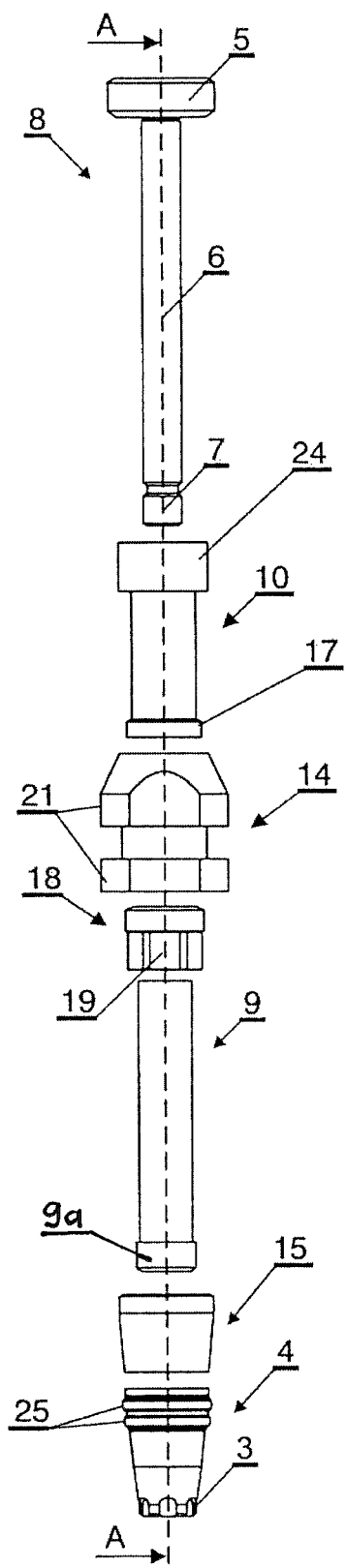
FIGS. 2A and 2B illustrate the individual parts of the impression jig shown in FIG. 1A in a side view and a sectional view, respectively.

The design and the operation of the impression jig according to the present invention will now be described with reference to a preferred embodiment shown in detail in FIGS. 1a to 9b.

As illustrated in FIGS. 1A to 2B, the major parts of the impression jig 1 according to the present invention includes a central screw 8, a tubular screw 11, a main body 16 formed of an upper member 14 and a lower member 15, a slide 18 and a head 4. As illustrated in FIG. 1B, at preparing a sample, the impression jig 1 is fixed in the implant 2 in a way that a positioning surface of the head 4 of the impression jig 1 fits into the a sleeve 20 formed on an inner surface of the implant 2 in a form-fitting, unrotatable manner. A central screw 8 is guided through the head 4 to tightly secure the impression jig to the implant 2.

Figure 2B:
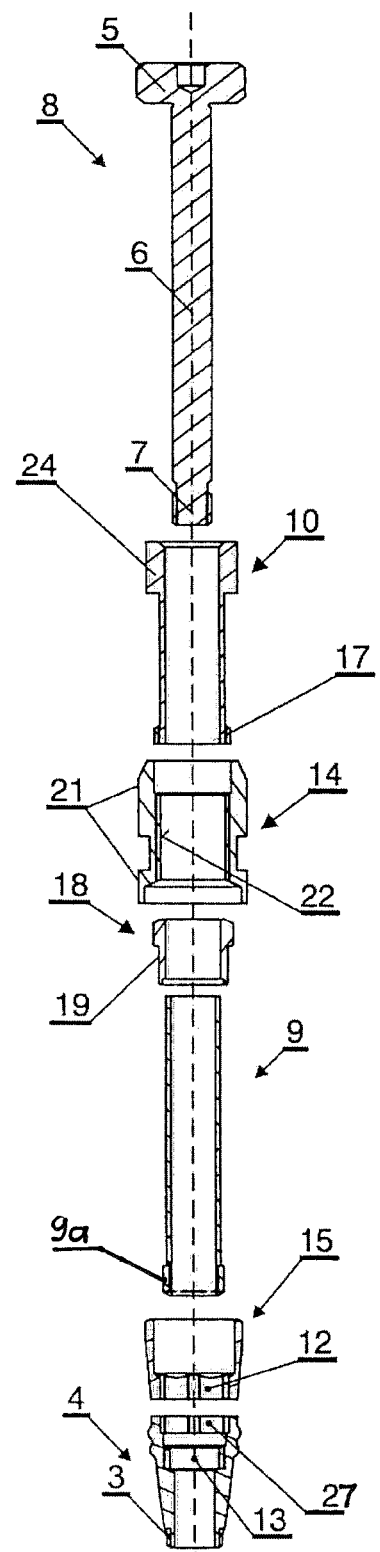
Figure 3:
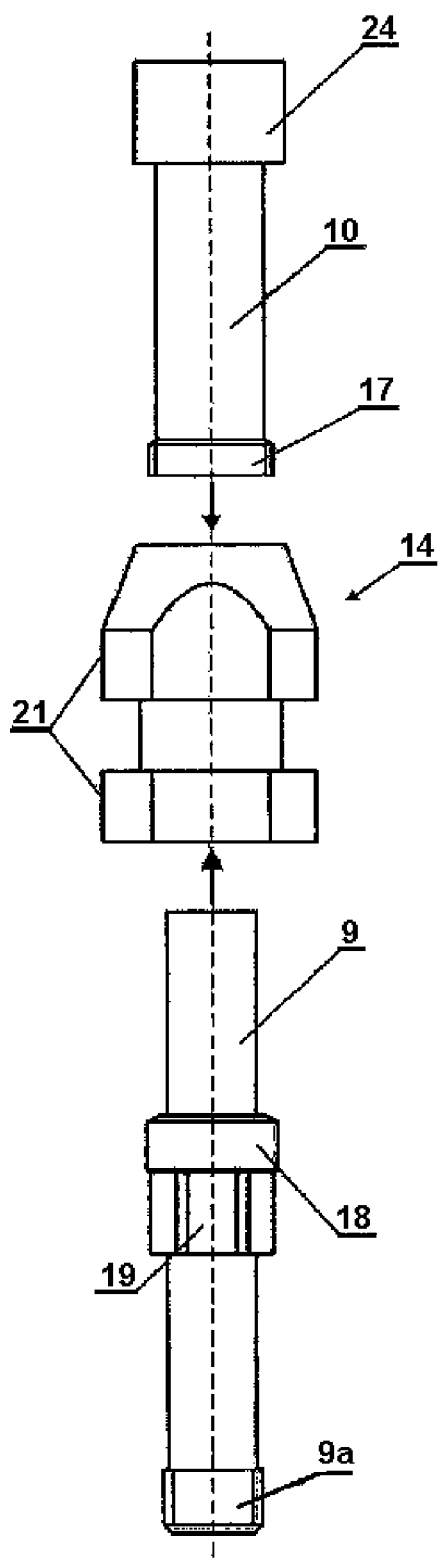
FIG. 3 shows the process of assembling the tubular screw, the upper member and the slide of the impression jig in a side view.
Figure 4A:
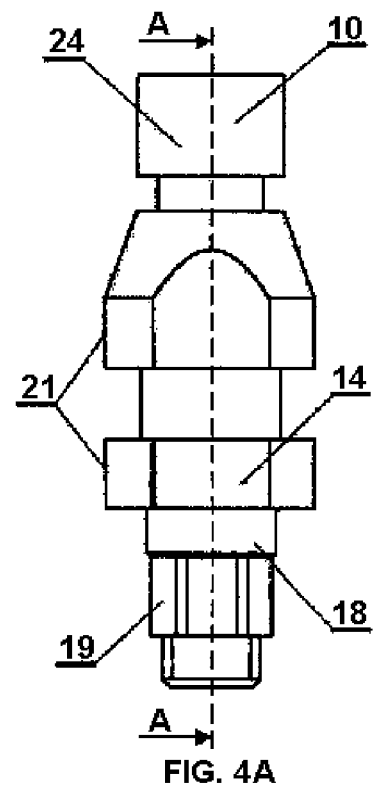
FIGS. 4A and 4B are a side view and a sectional view, respectively, of the tubular screw, the upper member and the slide of the impression jig after assembling.
Figure 4B:
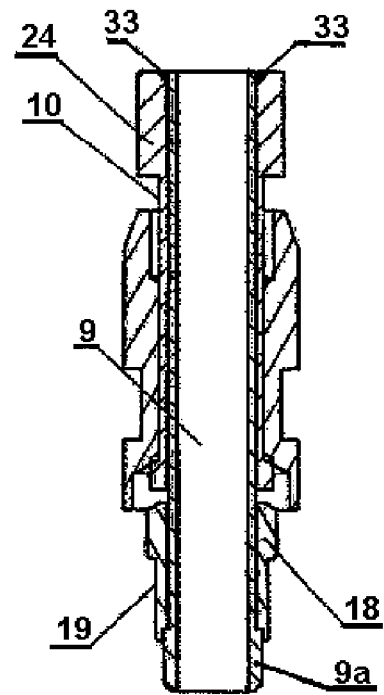
Figure 5:
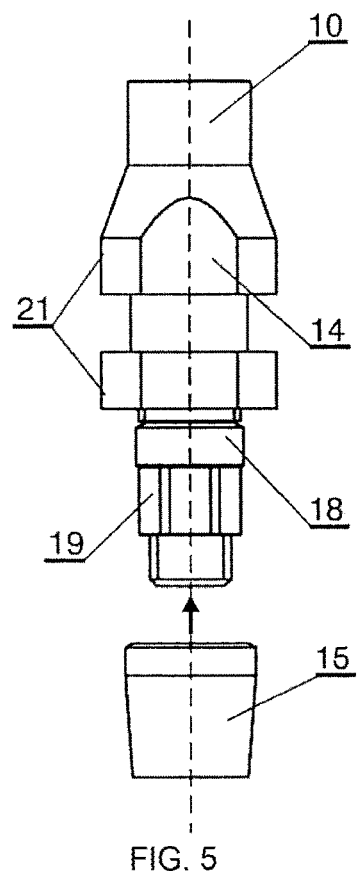
FIG. 5 shows the process of mounting the lower member to the impression jig unit shown in FIG. 4A, in a side view.
Figure 6:
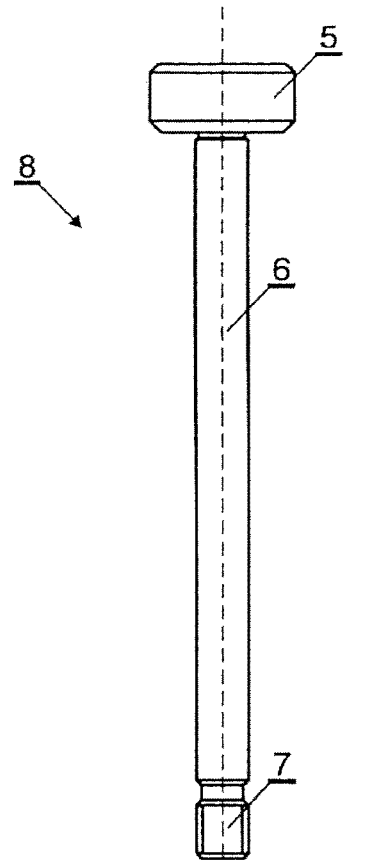
FIG. 6 illustrates a possible travel path of the slide within the lower member.
Figure 6:
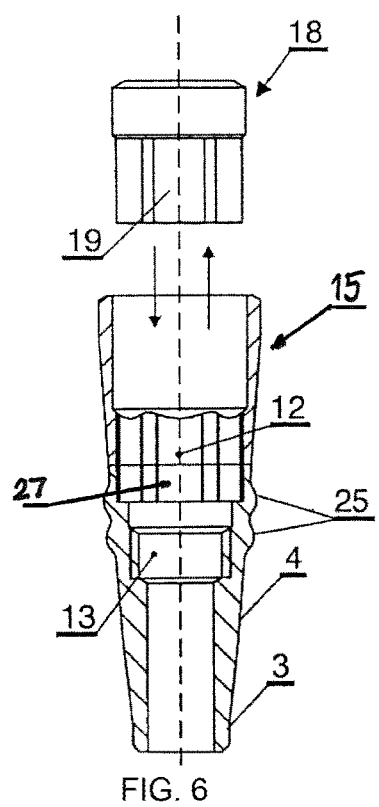
Figure 7:
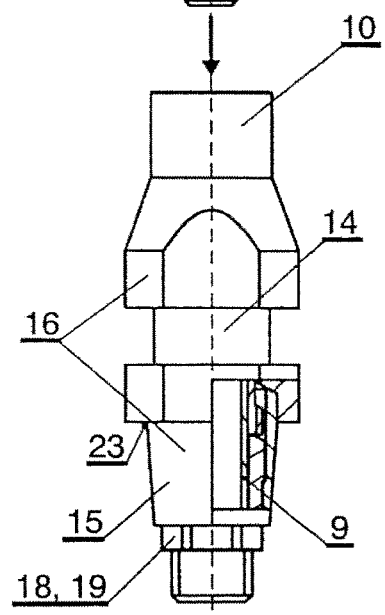
FIG. 7 shows the process of inserting the central screw into the unit shown in FIG. 5, partly in a side view and partly in a sectional view.

As shown in FIGS. 2A and 2B, the central screw 8 has a head 5, a shank 6 and a threaded end portion 7. The central screw 8 is secured by its end portion 7 to a threaded seat formed at the bottom of the implant 2, while a positioning end portion 3 of the head 4 is inserted into a positioning sleeve 20 of the implant in a form-fitting manner, thereby preventing the impression jig 1 from turning with respect to the dental implant 2. The length of the central screw 8 is dimensioned so that the threaded end portion 7 slightly over-project beyond the head 4 and be capable of engaging with the threaded seat of the dental implant 2, as it is illustrated in FIG. 2B.

The shank 6 of the central screw 8 can be led through an inner channel of a tubular screw 11 formed of a hollow upper screw member 10 and a hollow lower screw 9 member. The lower screw member 9 of the tubular screw 11 is preferably inserted into the an inner space of the upper screw member 10, and these two screw members are secured to each other in an unreleasable manner, for example by means of a weld 33 shown in FIG. 4B.

On an inner surface of the head 4, there is an inner positioning surface 12, and below it (i.e. towards the implant 2), there is a threaded seat 13 formed. At an upper end of the head 4, a curved flange is preferably formed to allow an easier disengagement of the impression jig at the upper end of the head 4 (i.e. separation of the main body 16 from the head 4) when the impression jig 1 is being removed from the dental implant 2.

Preferably, the lower screw member 9 and the upper screw member 10 are formed to mutually fit into each other in a way that an upper section of the lower screw member 9 is inserted into an inner channel of the upper screw member 10. Before assembling these two members, the upper screw member 10 is led through an upper member 14 of the tubular main body 16, the fixation of which in the resilient sampling material is assisted by a plurality of ribs 21 and/or corner cuts formed on an outer lateral surface thereof.

A head 24 of the upper screw member 10 leans against a flange of the upper end of the upper member 14 of the main body 16. At the end portion of the upper screw member 10 adjacent to the implant 2, there is a threaded part 17, also serving as a stop for a slide 18, is formed, and on the inner surface of the upper member 14, an inner threaded part 22 is formed to engage with a threaded part 17 of the upper screw member 10.

The slide 18 is arranged around the lower screw member 9. The slide 18 is prevented from sliding down along the lower screw member 9 by means of a threaded part 9a formed on the end portion of the lower screw member 9 adjacent to the implant 2, said threaded part also fitting into the threaded seat 13 of the head 4.

In a preferred embodiment of the impression jig shown in the drawings, the threaded part 9a of the lower screw member 9, the threaded part 17 of the upper screw member 10, and the inner thread 22 formed within the upper member 14 of the main body 16 are arranged with respect to each other so that at unscrewing the tubular screw 11, the threaded part 17 shall engage with the inner thread 22 even before the threaded part 9a releases from the threaded seat 13 of the head 4. In this way it is ensured that during its unscrewing the tubular screw 11 is continuously guided by threads. It is obvious for a person skilled in the art that engagement and disengagement of the head with/from the main body may also be carried out with any other design of the aforementioned parts.

The lower screw member 9 and the slide 18 are arranged in the lower member 15 of the main body 16 so that in its lower end position (i.e. when the tubular screw 11 is entirely screwed in) the outer positioning surface 19 formed on the lateral surface of the slide 18 fits to the inner positioning surface 12 formed in the lower member 15 and also to the positioning surface 27 formed on the upper end of the head 4. Hence, the slide 18 cannot turn within the lower member 15. However, the slide 18 can freely move in an axial direction within the head 4 and the lower member 15.

The upper member 14 and the lower member 15 of the main body 16 are secured to each other in an unreleasable way, for example by means of a weld 23 shown in FIG. 8B, thereby they functionally form a single integrated piece.

The positioning end portion 3 of the head 4 of the impression jig 1 is formed to engage with the positioning sleeve 20 of a dental implant 2 in a form-fitting manner. For example, when the positioning sleeve 20 of the implant 2 has a hexagonal cross-section, the positioning end portion of the head 4 is also formed with a precisely matching hexagonal cross-section.

The positioning surface 27 of the head 4 and the inner positioning surface 12 of the lower member 15 of the main body 16 may be formed as a socket-type sleeve with a hexagonal, star-shaped, torx etc. cross-section, for example. The outer positioning surface 19 of the slide 18 is formed to fit to these positioning surfaces in a form-fitting manner, so it is preferred that the positioning surface 19 is also formed correspondingly, for example with a shape of an Allen-key, or with a star or torx cross-section. The inner positioning surfaces 12 and 27, and the outer positioning surface 19 are always formed to engage with each other in form-fitting manner so that they prevent the main body 16 from turning with respect to the head 4 when the slide 18 is partly or entirely inserted into the outer end portion of the head 4. The rotation of the main body 16 around the central axis of the impression jig 1, with respect to the head 4 (during the preparation of the sample at an engaged position of the two parts) may be assisted by any other surface design. For example, to this end, a plurality of ribs may be formed on the slide 18 and a plurality of respective grooves may be formed on the inner surface of the lower member 15 and on the inner surface of the outer end portion of the head 4.

The inner positioning surface 12 is formed within the lower member 15 of the main body 16 so that at an upper end position of the slide 18, when the hollow screw 11 is unscrewed to a maximum extent, the outer positioning surface 19 of the slide 18 still aligns with the inner positioning surface 12 of the lower member 15 in a form-fitting manner, thus at the removal of the impression jig 1 from the implant 1 (and also thereafter) the slide 18 cannot turn within the lower member 15 even accidentally.

Figure 9A:
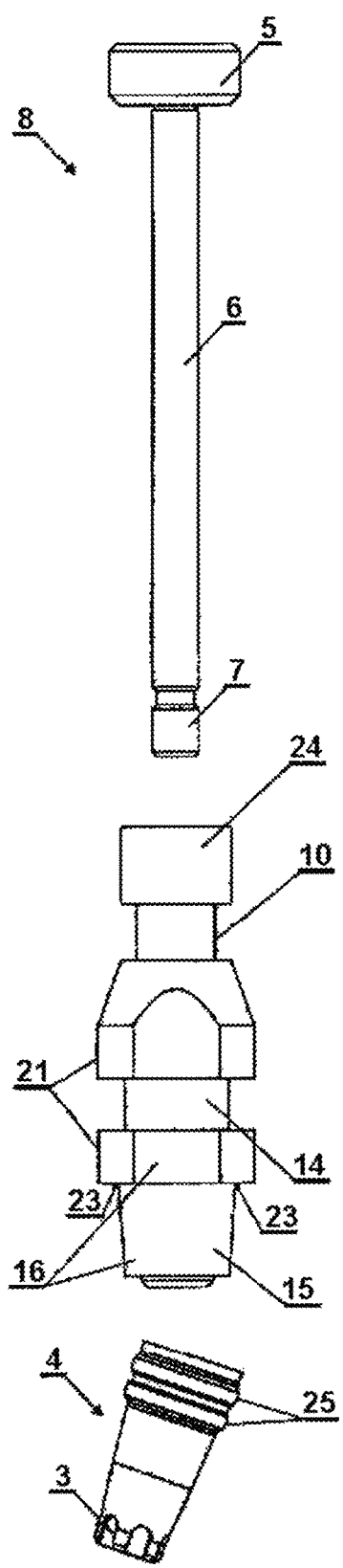
FIGS. 9A and 9B are a side view and a sectional view, respectively, of the lower member and the assembled upper member of the impression jig, as well as the central screw in a disengaged state.
Figure 9B:
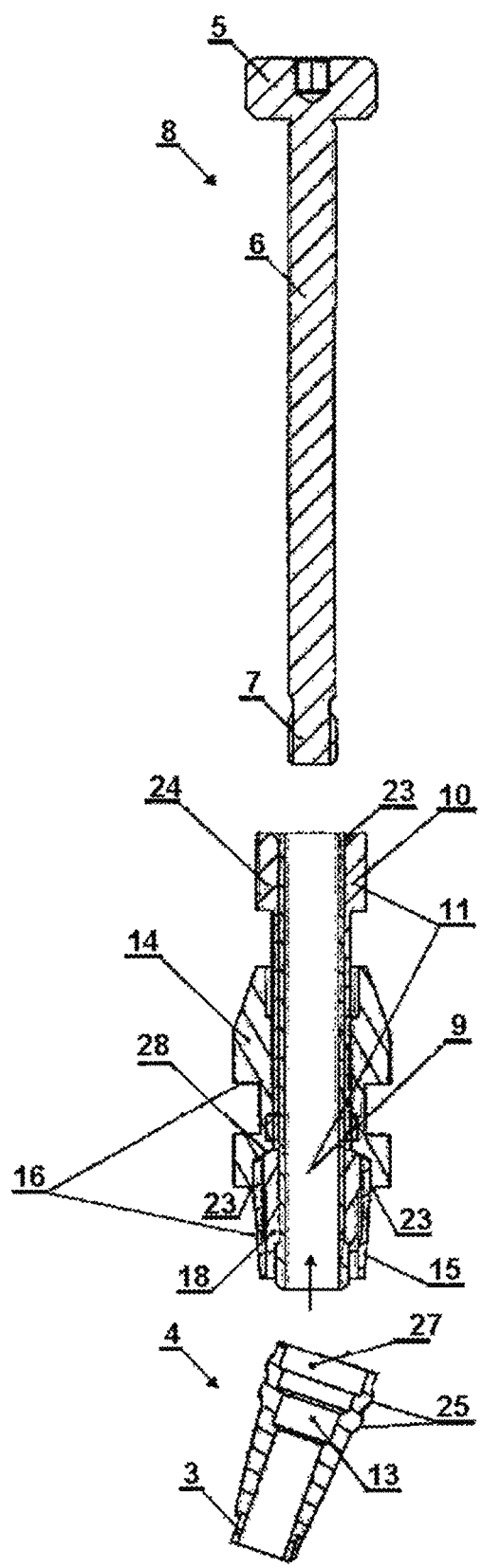

The upper end position of the slide 18 is preferably provided by a stop 28 formed on the wall of the inner channel of the upper member 14, as it can be best seen in FIG. 9B.

When starting screwing the tubular screw 11, the slide 18 staying in its upper end position is preferably pushed downwards by the threaded part 17 of the upper screw member 10 of the tubular screw 11 while it is moving downwards, and the slide 18 is being pushed downwards until its lower end leans against the seat of the positioning surface 27 in the head 4, and as it can be seen in FIG. 8B, for example.

When unscrewing the tubular screw 11, it is preferred that the lower end portion of the slide 18 leans against the threaded part 9a of the lower screw member 9, and the tubular screw 11, while it is moving upwards, draws the slide 18 with itself until the upper end portion of the slide 18 leans against the stop 17 formed within the inner channel of the upper member 14 of the main body 16. It is obvious for a person skilled in the art that in its entirely screwed position of the tubular screw 11, the function of displacing the slide 18, which provides a locking mechanism between the head 4 and the main body 16, and the function of providing the end positions of the slide 18 inside the main body may also be provided in other ways as well. The key feature is that in its lower end position the slide 18 should be capable of preventing the head 4 from turning away with respect to the main body 16 and not blocking any displacement and/or rotation of the head 4 with respect to the main body 16 at its upper end position, while the slide 18 itself is still prevented from turning relatively to the main body 16. This principle of operation allows an extremely accurate copying of the spatial orientation of the dental implants.

It is preferred that the outer lateral surface 21 of the upper member 14 of the main body 16 is at least partly provided with ribs and/or corner cuts as it can be seen in FIGS. 8A and 9A, for example.

The head 5 of the central screw 8 may, for example, be a socket-type head or a cornered head as it can be seen in FIG. 2B, for example.

In the following, the use of the impression jig according to the present invention will be described with reference to FIGS. 10A to 10E. At the preparation of a sample, an assembled impression jig 1, like the one shown in FIG. 1A, is secured to the implant 2 in a way as shown in FIG. 1B. In this step the positioning end portion 3 of the head 4 is fitted into the positioning sleeve 20 of the dental implant 2, and then the end portion 7 of the central screw 8 is secured to the threaded seat of the implant 2 by screwing the central screw 8.

In the case where multiple impression jigs are to be secured to multiple dental implants 2 respectively, the impression jigs 1 are preferably fixed together by means of a conventional fastening material, such as Pattern Resin™ sampling material or any other material providing a stronger binding effect. Using this fastening material, the upper members 14 of the main bodies 16 of the impression jigs 1 are secured to each other in a way that the main bodies 16 of the impression jigs 1 can not move relative to each other at the subsequent sampling operations either.

Figure 10A:
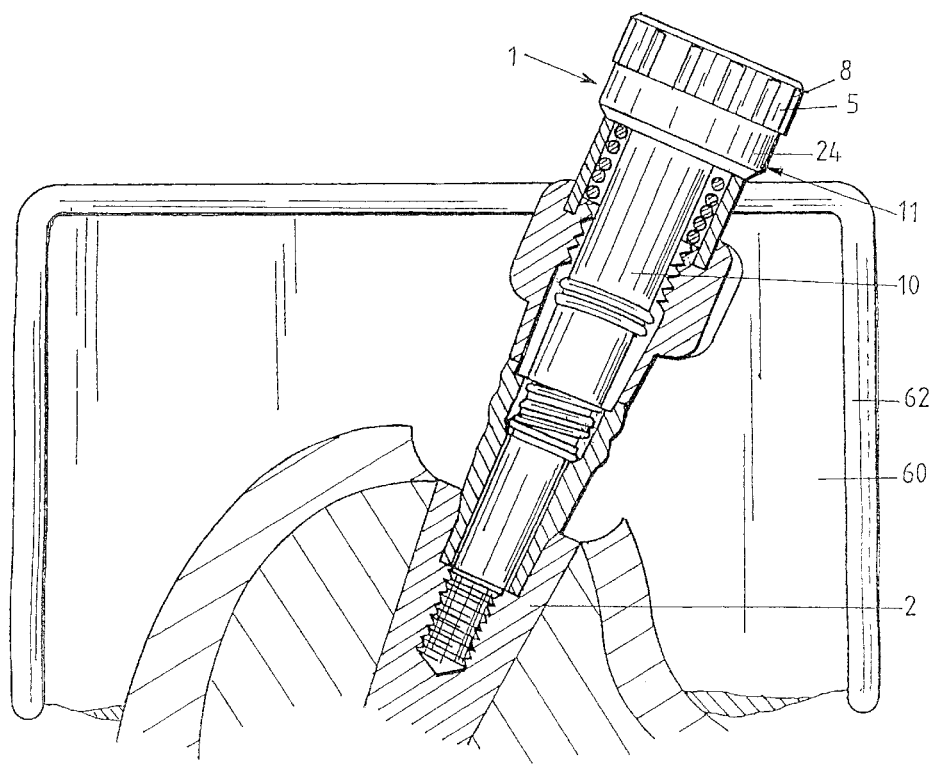
FIGS. 10A to 10E illustrate the major steps of a process of removing the impression jig of the present invention from a dental implant, partly in a side view and partly in a sectional view.
Figure 10B:
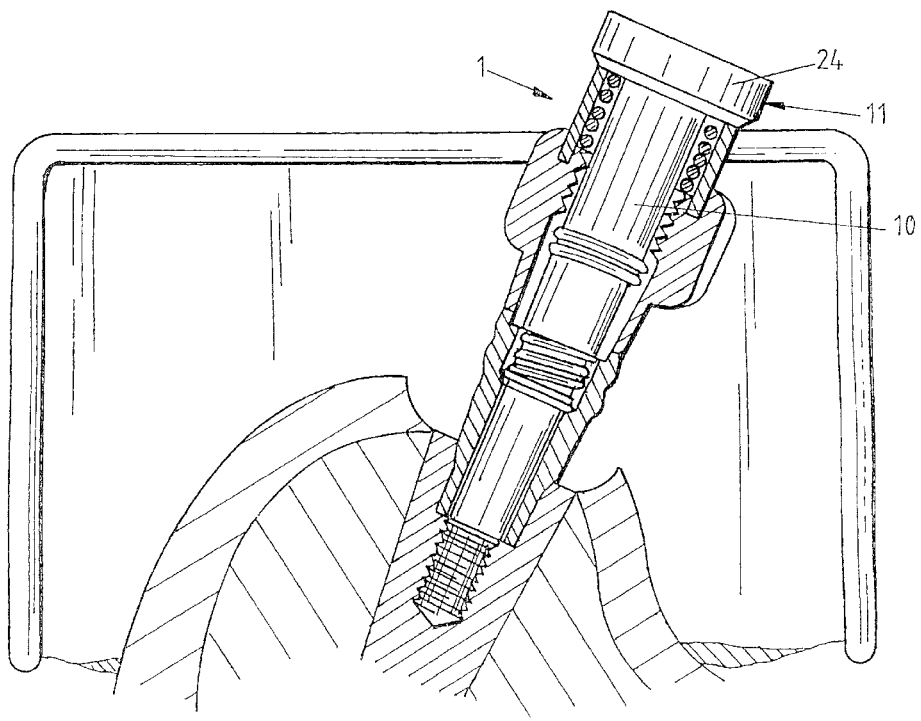
Figure 10C:
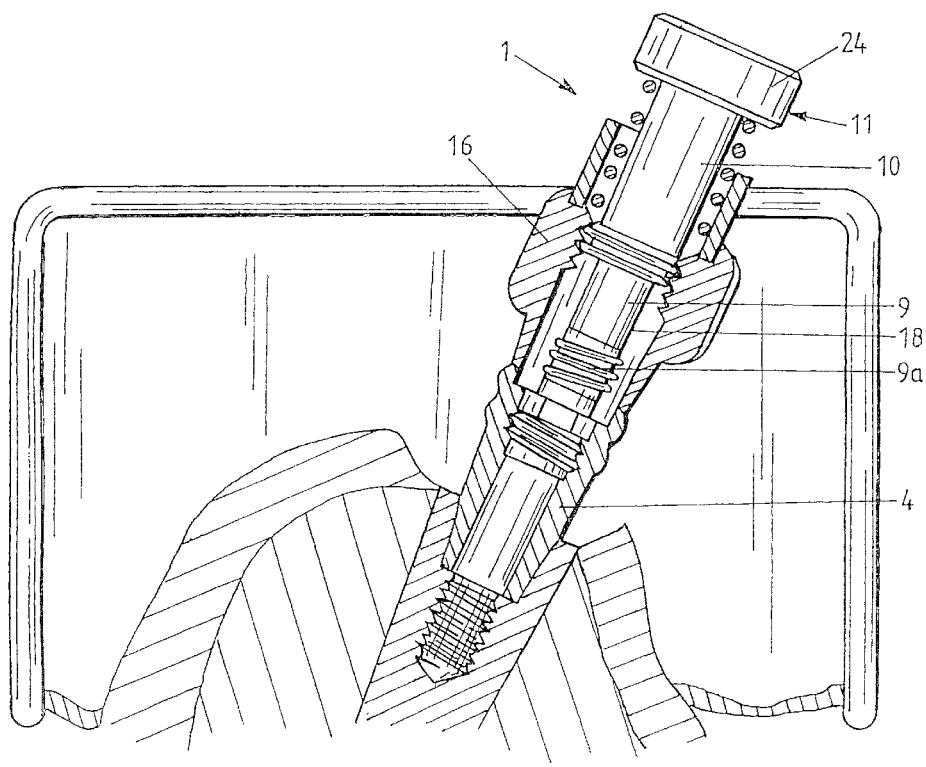

Then a sampling material 60, which is initially a plastically deformable or slightly resilient material that can be hardened off by using heat or UV light, is put into an open tray 62 and then the space between the impression jigs 1 is filled with the sampling material 60 in a way that the heads 5 of the central screws 8 of the impression jigs 1 and the heads 24 of the upper screws 10 of the tubular screws 11 remain exposed. This situation is shown in FIG. 10A.

Once the sampling material 60 has hardened off, the central screw 8 is unscrewed from the threaded seat formed on the bottom of the dental implant 2 and entirely removed from the impression jig 1. This situation can be seen in FIG. 10B. In this case, the tubular screw 11 can be unscrewed.

Next the tubular screw 11 is unscrewed by rotating the head 24. During this operation the threaded part 9a of the lower screw member 9 of the tubular screw 11, which has provided an engagement with the head 4 so far, on the one hand, and always prevents the slide 18 from sliding down, on the other hand, gets unscrewed from the head 4, while continuously lifting the slide 18 out of the head 4.

Before the lower screw member 9 of the tubular screw 11 is entirely unscrewed from the head 4, the threaded part 17 of the upper screw member 10 starts being screwed into the inner threaded part 22 formed inside the upper member 14 of the tubular screw 11. While the tubular screw 11 is getting further screwed, the lower screw member 9 gets disengaged from the head 4 and then it will be coupled only to the main body 16 by threads.

The tubular screw 11 is to be unscrewed only until its lower end portion is entirely released from the head 4, whereby the slide 18 also gets outside the head 4. At this position the form-fitting and rotation-free engagement between the upper body 16 and the head 4 due to the slide 18 ceases, and the main body 16 and the head 4 can be disengaged along their coupling surfaces and they can move relatively to each other even in a lateral direction or they can even turn away. The situation where the tubular screw 11 is fully unscrewed position can be seen in FIG. 10C. In this situation the slide 18 leans against the stop formed inside the main body 16.

In the next step, the sampling tools, including the sampling material 60, the one or more main bodies 16 and the one or more associated heads 4, all secured in the sampling material, can be removed from the dental implants 2 as a single piece in a way that during this operation the orientations of the one or more impression jigs 1 with respect to the sampling material, or in the case of using multiple impression jigs 1 at the same time, the mutual orientations of the impression jogs 1, do not change relative to each other.

Figure 10D:
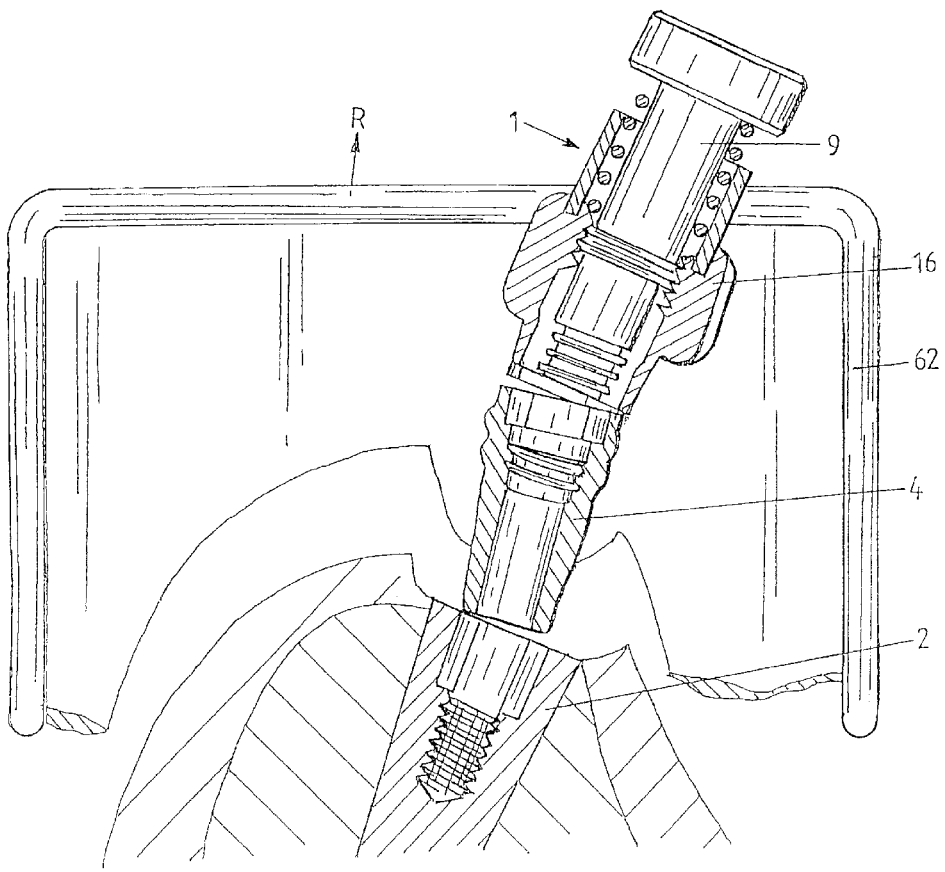

Since at this time there is no rigid connection between the heads 4 and the main bodies 16 any longer due to the plastically deformable or resilient sampling material 60, any one of the individual heads 4 can slightly move with respect to its associated main body 16 at the removal of the sampling material, which allows the impression jigs 1 to move outwards substantially along a removal direction R even if the axial direction of any one of the dental implants 2 differs from the moving direction of the open tray 62 to some extent, this latter direction corresponding to the moving direction of the main bodies 16 of the impression jigs 1. As a result, the stressing forces between the heads 4 and the implants 2 can be reduced to a minimum level, which makes the removal of the sampling material, and also the main bodies 16 and the heads 4 secured therein, from the dental implants easier, on the one hand, and produces a reduced mechanical load on the implants 2, on the other hand, thereby causing less damage to them. The last moment of the removal of an impression jig 1 from a dental implant 2 is illustrated in FIG. 10D. At this moment the head 4 is slightly tilted with respect to the main body 16, as well as to the dental implant 2 due to the difference between the axial direction of the implant 2 and the direction R of removal of the impression jig 1.

Figure 10E:
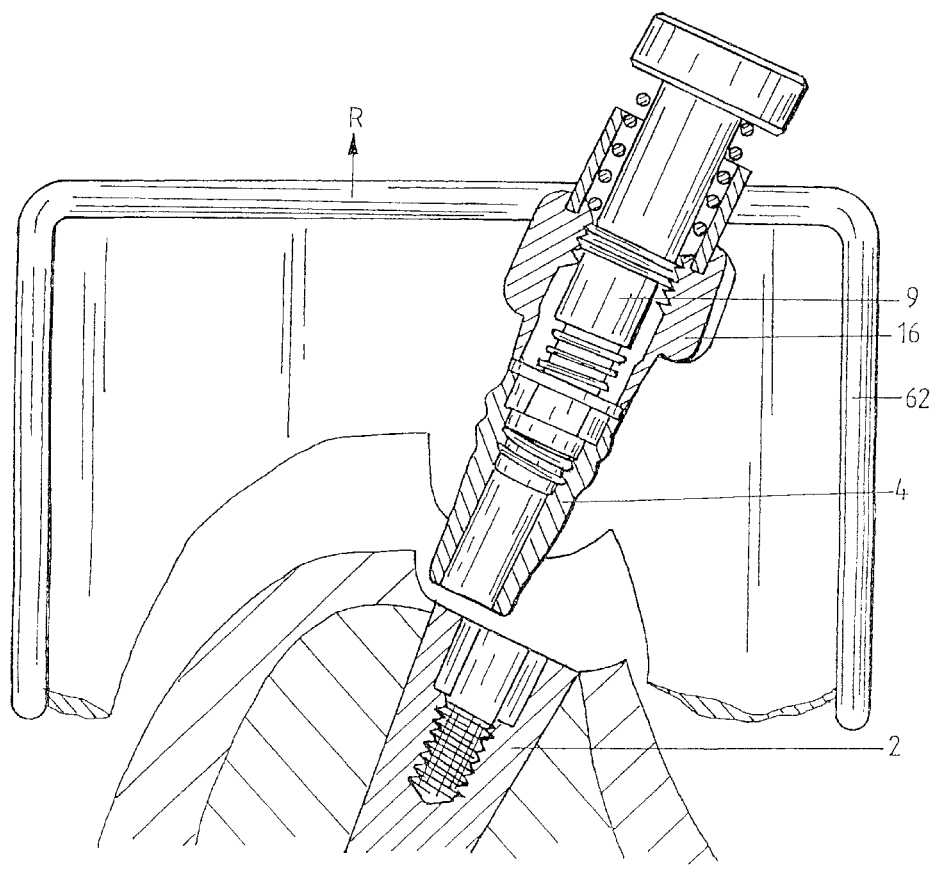

After separation, due to the resiliency of the sampling material 60, the head 4 returns substantially into its initial orientation, i.e. in a direction substantially parallel to the axial direction of the dental implant 2, while it gets into a substantially coaxial orientation with respect to the main body 16 as it can be seen in FIG. 10E.

In a dental prosthetic laboratory, the tubular screws 11 residing in the main bodies 16 carried by the sampling material 60 are entirely screwed in again, and the central screws 8 are inserted into the tubular screws 11, and then the secondary dental implants are screwed over the threaded end portions of the central screws 8. When a tubular screw 11 is entirely screwed in, the slide 18 partly slides into the outer end portion of the head 4 again, and there it engages with the head 4 in a form-fitting manner. Since the slide 18 can intrude into the head 4 only at specific discrete positions due to its positioning surfaces, any possible minor remaining displacements and/or rotations of the head 4 with respect to the main body 16 (which may happen at the removal of the sampling material 60) can be perfectly compensated at the guided re-engagement of the main body 16 and the head 4. Due to this fact, in the dental prosthetic laboratory, the secondary implants accommodate exactly in the same angular positions and spatial orientations as the implants residing in the bone of the patient, so the impression jigs according to the present invention allow a very precise spatial modeling of the patient's implants.

Although in the foregoing the impression jig according to the present invention was described with reference to the drawings through a dental implantation technique, the invention is not limited to this field of application, but it can be also used for a precise modeling of other implants in an analogous way.

It is also noted that in the present description, the terms "lower" and "upper" are only used as relative terms for an easier understanding of the structure of the invention described through the preferred embodiment that are shown in the drawings, and it is obvious for those skilled in the art how to interpret these terms for an impression jig extending in any other (e.g. reversed) spatial orientation.

Finally, it is noted that the preferred embodiment described above and shown in the drawings is only a preferred embodiment and the invention is not limited to this preferred embodiment. The impression jig according to the present invention may have numerous embodiments within the scope of the invention defined by the claims.

The invention claimed is:

1. An impression jig comprising:
   a main body having an inner channel and a head having an inner channel and adapted for being releasably attached to said main body,
   wherein the inner channel of the main body is provided with threads and at its lower end portion, with an inner positioning surface, and
   wherein the inner channel of the head is provided with threads and at its upper end portion, with an inner positioning surface,
   a tubular screw adapted for guiding through the inner channel of the main body and into the inner channel of the head, said tubular screw having an inner channel, and wherein an outer surface of the tubular screw is provided with first threads at a lower end thereof and with second threads at a predetermined distance from said lower end,
   a central screw, the shank of which is adapted for guiding through the inner channels of the tubular screw and the head, wherein a lower end portion of the shank is provided with threads, and wherein said shank is longer than the total length of the main body and the head when engaged with each other, and
   a slide movable within the inner channel of the main body between a first position and a second position in an axial direction by means of said tubular screw, wherein the slide comprises a positioning surface on its outer side at a lower part thereof,
   wherein in its first position, the slide resides partly in the main body and partly in the head, and the positioning surface of the slide engages with the upper positioning surface of the head in a form-fitting manner, and
   wherein in its second position, the whole slide resides in the inner channel of the main body, and the positioning surface of the slide engages with the inner positioning surface of the main body.

2. The impression jig of claim 1, wherein when the slide is in its first position, the first threads of the tubular screw engage with an upper threaded part of the main body.

3. The impression jig of claim 1, wherein when the slide is in its second position, the second threads of the tubular screw engage with the threads of the inner channel of the main body.

* * * * *